US012712101B2

(12) United States Patent
Zetterer et al.

(10) Patent No.: US 12,712,101 B2
(45) Date of Patent: Aug. 18, 2026

(54) ELECTRICAL FEEDTHROUGH

(71) Applicant: Schott AG, Mainz (DE)

(72) Inventors: Thomas Zetterer, Landshut (DE); Linda Johanna Bartelt, Landshut (DE); Jonas Baehr, Munich (DE); Robert Hettler, Kumhausen (DE); Jochen Herzberg, Allhaming (AT); Ricarda Krechel, Sprendlingen (DE); Ina Mitra, Stadecken-Elsheim (DE); Ina Filbert-Demut, Pilsting (DE)

(73) Assignee: SCHOTT AG, Mainz (DE)

( * ) Notice: Subject to any disclaimer, the term of this patent is extended or adjusted under 35 U.S.C. 154(b) by 234 days.

(21) Appl. No.: 18/436,749

(22) Filed: Feb. 8, 2024

(65) Prior Publication Data

US 2024/0186035 A1 Jun. 6, 2024

Related U.S. Application Data

(63) Continuation of application No. PCT/EP2022/072193, filed on Aug. 8, 2022.

(30) Foreign Application Priority Data

Aug. 10, 2021 (DE) ..................... 10 2021 120 789.4
Aug. 8, 2022 (WO) ................ PCT/EP2022/072193

(51) Int. Cl.
*H01B 17/62* (2006.01)
*C03C 3/091* (2006.01)
(Continued)

(52) U.S. Cl.
CPC ............ *H01B 17/62* (2013.01); *C03C 3/091* (2013.01); *H01B 3/087* (2013.01); *H01R 13/405* (2013.01); *A61N 1/3754* (2013.01)

(58) Field of Classification Search
None
See application file for complete search history.

(56) References Cited

U.S. PATENT DOCUMENTS 4,280,932 A * 7/1981 Borom .................... C03C 3/145 338/238
5,104,755 A 4/1992 Taylor et al.
(Continued)

FOREIGN PATENT DOCUMENTS

DE 690 28 579 T2 3/1997
DE 10 2018 220 118 A1 5/2020
KR 10-2019-0094611 A 8/2019

OTHER PUBLICATIONS

English machine translation of Korean Patent No. 10-2019-0094611 dated Aug. 14, 2019 (20 pages).
(Continued)

*Primary Examiner* — Krystal Robinson
(74) *Attorney, Agent, or Firm* — TAYLOR & EDELSTEIN, PC

(57) ABSTRACT

A feedthrough includes: a main body including at least one passage opening running through the main body, the main body including titanium or a titanium alloy; an insulation material accommodated in the at least one passage opening running through the main body, the insulation material including glass, the insulation material having a contact angle of less than 90 degrees at least in a plurality of regions of the insulation material with respect to the main body; and at least one electrical conductor extending through the insulation material accommodated in the at least one passage opening.

20 Claims, 2 Drawing Sheets

(51) Int. Cl.

*H01B 3/08* (2006.01)
*H01R 13/405* (2006.01)
*A61N 1/375* (2006.01)

(56) References Cited

U.S. PATENT DOCUMENTS

| | | | | |
|---|---|---|---|---|
| 5,306,581 | A * | 4/1994 | Taylor | H01B 17/305 429/184 |
| 5,531,003 | A | 7/1996 | Seifried et al. | |
| 5,821,011 | A * | 10/1998 | Taylor | H01M 50/186 174/61 |
| 6,058,782 | A * | 5/2000 | Kurtz | G01L 9/0054 73/727 |
| 6,159,560 | A | 12/2000 | Stevenson et al. | |
| 6,274,252 | B1 * | 8/2001 | Naugler | C03C 27/02 403/30 |
| 6,300,716 | B1 | 10/2001 | Honda | |
| 6,670,074 | B2 * | 12/2003 | Spillman | H01M 50/191 429/185 |
| 6,759,163 | B2 * | 7/2004 | Frysz | H01M 50/186 429/185 |
| 9,206,672 | B2 | 12/2015 | Cooley et al. | |
| 9,956,322 | B2 | 5/2018 | Pichler-Wilhelm et al. | |
| 10,224,521 | B2 * | 3/2019 | Kroll | B23K 15/04 |
| 2003/0096162 | A1 * | 5/2003 | Lasater | H01J 5/34 29/623.2 |
| 2008/0085451 | A1 | 4/2008 | Freitag et al. | |
| 2016/0311720 | A1 | 10/2016 | Suffner | |
| 2017/0222195 | A1 | 8/2017 | Hartl | |
| 2019/0084871 | A1 * | 3/2019 | Mitra | C03C 27/02 |

OTHER PUBLICATIONS

Notification of the Transmission of the International Search Report and Written Opinion of the International Search Authority or Declaration dated Nov. 14, 2022 for International Application No. PCT/EP2022/072193 (11 pages).

* cited by examiner

ELECTRICAL FEEDTHROUGH

CROSS REFERENCE TO RELATED APPLICATIONS

This is a continuation of PCT application no. PCT/EP2022/072193, entitled "ELECTRICAL FEEDTHROUGH", filed Aug. 8, 2022, which is incorporated herein by reference. PCT application no. PCT/EP2022/072193 claims priority to German patent application no. 10 2021 120 789.4, filed Aug. 10, 2021, which is incorporated herein by reference.

BACKGROUND OF THE INVENTION

1. Field of the Invention

The present invention relates to an electrical feedthrough.

2. Description of the Related Art

Electrical feedthroughs with an external metallic main body and an internal glass component that serves as an insulator (glass-metal feedthroughs), through which one or more conductors extend, are used in numerous applications, especially for hermetic wall sections, for instance of housing elements. Corresponding components are used, for example, in the field of medical technology, for example in implantable medical devices (IMDs), in the field of oil and/or gas exploration, in the field of aviation, and in many other fields; while it may be necessary depending on the field of use to take account of different profiles of requirements, commonalities exist with regard to optimization and further development of known solutions.

In general, it is desirable, for example, and is an object of the present invention to increase the stability of such feedthroughs with regard to physical and/or chemical influences, to improve the integrity of the insulation material with respect to the surrounding main body and/or with respect to the electrical conductor that extends through the insulation material, and to optimize the production of such feedthroughs and/or to lower production costs.

What is needed in the art is to better match the properties of the main body, the insulation material and/or the electrical conductor that extends through the insulation material to one another and this especially includes the choice of materials or compositions of the materials of the individual components.

What is also needed in the art is, with regard to the use of feedthroughs in medical technology, that the components used are non-toxic when they can come into contact at least temporarily or even permanently (in the case of implants) with body fluids and this relates not only to the main body and the electrical conductors but in particular to the glasses (owing to leaching effects), and it may therefore especially be the case here that cytotoxicity tests are conducted beforehand, before, for example, further qualification tests are conducted for medical devices and implants, for example.

SUMMARY OF THE INVENTION

The present invention relates to an electrical feedthrough with a metal including a main body that accommodates a glass including insulation material with an electrical conductor that extends through it.

The present invention provides a feedthrough including a main body with at least one passage opening running through the main body, and also an insulation material accommodated in the passage opening running through the main body, and at least one electrical conductor extending through the insulation material accommodated in the passage opening, wherein the main body includes titanium or a titanium alloy and the insulation material includes glass, and wherein the insulation material has a contact angle of less than 90 degrees at least in some regions with respect to the main body.

By the provision of a main body including or composed of titanium or a titanium alloy (e.g. titanium grade 1, titanium grade 2, titanium grade 3, titanium grade 4 or titanium grade 5, especially TiAl6V4 alloy), of an insulation material including or composed of glass and of a contact angle of below 90 degrees at least in some regions, it is especially possible to improve the integrity of the insulation material with respect to the surrounding main body or to increase the stability of the feedthrough to physical and/or chemical influences. In particular, it is possible to achieve higher mechanical durability. With a contact angle of below 90 degrees, it is especially possible to achieve improved fusion and, for example, to prevent accumulation of liquids at the material transition, such that, for example, stress cracks can be avoided. With the use of titanium or titanium alloys, it is possible to enable high corrosion resistance, high strength, especially coupled with relatively low density, and/or avoidance of cytotoxicity, especially for use in the medical sector.

In relation to the transition from the insulation material to the main body, it may be the case that the contact angle of the insulation material with respect to the main body is between 56 and 86 degrees, optionally between 62 and 84, optionally between 68 and 82 degrees, optionally between 70 and 80 degrees.

Moreover, in relation to the transition from the insulation material to the electrical conductor, it may be the case that the insulation material at least in some regions has a contact angle with respect to the electrical conductor of between 56 and 86 degrees, optionally between 62 and 84, optionally between 68 and 82 degrees, optionally between 70 and 80 degrees.

The electrical conductor may include or consist of a metal, for example materials such as NiFe alloys, niobium, platinum, platinum alloys and/or molybdenum. The electrical conductor may have a coefficient of thermal expansion of between 5 and 9 ppm/K, optionally between 7 and 9 ppm/K. In conjunction with a main body including or composed of titanium, it is possible thereby to provide a pressure vitrification, which can increase mechanical robustness.

The insulation material optionally provides an electrical insulation of at least 1 GOhm, especially at temperatures of 175° C. or 200° C. Option is further given to a breakdown resistance of at least 1 V/μm, especially at those temperatures.

In relation to the glass composition, it may be the case that the glass of the insulation material has a glass composition containing $B_2O_3$ and $SiO_2$, where the ratio of the proportion of $B_2O_3$ in percent by weight to the proportion of $SiO_2$ in percent by weight is at least 0.45, optionally at least 0.47, more optionally at least 0.49.

It is possible here that the glass of the insulation material has a glass composition containing $B_2O_3$ and $SiO_2$, where the ratio of the proportion of $B_2O_3$ in percent by weight to the proportion of $SiO_2$ in percent by weight is between 0.45 and 0.65, optionally between 0.47 and 0.64, optionally between 0.49 and 0.63.

In relation to the glass composition, it may also be the case that the glass of the insulation material has a glass composition containing $B_2O_3$, where the proportion of $B_2O_3$ in the glass composition is at least 21 percent by weight, optionally at least 22 percent by weight, optionally at least 23 percent by weight or at least 25 percent by weight.

It is possible here that the glass of the insulation material has a glass composition containing $B_2O_3$, where the proportion of $B_2O_3$ in the glass composition is between 21 and 33 percent by weight, optionally between 22 and 32 percent by weight, optionally between 23 and 31 percent by weight or between 25 and 30 percent by weight.

In some cases, the use of titanium or titanium alloys in relation to chemical reactions can give rise to the peculiarity that the glass-forming oxide $SiO_2$ reacts with titanium to give titanium silicide, which can result in detachment phenomena at the glass-metal contact zone. This problem can especially be alleviated or avoided by way of the above figures for the glass composition. In particular, it is possible by way of the figures given for $B_2O_3$ to suppress this reaction and to lead to a TiB layer that leads to more chemically and mechanically stable compounds between a titanium-including component and the glass.

In principle, it should be taken into account that titanium is strongly reactive. The abovementioned glass compositions can alleviate or prevent reaction of the titanium on melting (for example at melting temperatures of, for example, 700 to 900° C.) with $SiO_2$ to give titanium silicide, and accompaniment of this reaction by blistering at the interface, for example.

The glass of the insulation material may have a softening temperature of not more than 750° C., optionally not more than 700° C., optionally not more than 680° C.

The glass of the insulation material may have a sphere temperature of not more than 850° C., optionally not more than 800° C., optionally not more than 780° C.

The glass of the insulation material may have a hemisphere temperature of not more than 950° C., optionally not more than 900° C., optionally not more than 850° C.

The glass of the insulation material may have a flow temperature of not more than 1050° C., optionally not more than 1000° C., optionally not more than 950° C.

For vitrifications in titanium, it should be taken into account that pure titanium has a phase transition temperature of 880° (alpha/beta). This temperature is higher for titanium grade 5 (TiAl6V4), but the reaction mechanisms at the interface to the glass are the same.

The aforementioned properties, for example in the case of a glass composition with the abovementioned $B_2O_3$ contents, can optionally enable the boron content to be sufficiently maintained on melting.

Moreover, the glass of the insulation material may optionally be stable on storage in saline solution at 37.5° C.

Further advantageous components with regard to the glass composition are specified hereinafter.

For example, it may be the case that the glass of the insulation material has a glass composition containing $Al_2O_3$, where the proportion of $Al_2O_3$ in the glass composition is at least 3 percent by weight, optionally at least 7 percent by weight, optionally at least 9 percent by weight.

It is possible here that the glass of the insulation material has a glass composition containing $Al_2O_3$, where the proportion of $Al_2O_3$ in the glass composition is between 3 and 17 percent by weight, optionally at least 7 and 16.5 percent by weight, optionally at least 9 and 15 percent by weight.

The aforementioned values can advantageously increase chemical stability in particular.

Moreover, the glass of the insulation material may have a glass composition containing $Na_2O$, where the proportion of $Na_2O$ in the glass composition is at least 10 percent by weight, optionally at least 12 percent by weight.

There follows a specification of further components that are advantageously present merely to a limited degree in relation to the glass composition.

For example, it may be the case that the glass of the insulation material has a glass composition containing CaO, where the proportion of CaO in the glass composition is at most 11 percent by weight, optionally at most 10 percent by weight, optionally at most 7 percent by weight.

In addition, the glass of the insulation material may have a glass composition containing $TiO_2$, where the proportion of $TiO_2$ in the glass composition is at most 10 percent by weight, optionally at most 5 percent by weight, optionally at most 4.5 percent by weight.

There follows a specification of further components that are advantageously not present, essentially not present or present merely to a limited degree in relation to the glass composition.

For example, it may be the case that the glass of the insulation material has a glass composition containing no $K_2O$ or containing $K_2O$, where the proportion of $K_2O$ in the glass composition is less than 7 percent by weight, optionally less than 5 percent by weight, optionally less than 3 percent by weight.

The glass of the insulation material may also have a glass composition containing no $LiO_2$ or containing $LiO_2$, where the proportion of $LiO_2$ in the glass composition is less than 2 percent by weight, optionally less than 1 percent by weight, optionally less than 0.5 percent by weight. This may be advantageous for reasons of cost among others. Moreover, this may be advantageous with regard to the avoidance of unwanted reactions with pharmaceuticals.

It may further be the case that the glass of the insulation material has a glass composition containing no MgO or containing MgO, where the proportion of MgO in the glass composition is less than 10 percent by weight, optionally less than 6.5 percent by weight, optionally less than 5 percent by weight.

The glass of the insulation material may also have a glass composition containing no $ZrO_2$ or containing $ZrO_2$, where the proportion of $ZrO_2$ in the glass composition is less than 0.9 percent by weight, optionally less than 0.5 percent by weight, optionally less than 0.1 percent by weight. This can advantageously prevent, for example, reduction in the glass viscosity and improve vitrification. Furthermore, this may be advantageous with regard to costs.

It may be the case that the glass of the insulation material has a glass composition containing no $La_2O_3$ or containing $La_2O_3$, where the proportion of $La_2O_3$ in the glass composition is less than 1.5 percent by weight, optionally less than 1 percent by weight, optionally less than 0.5 percent by weight. This may be advantageous for reasons of cost among others.

It may further be the case that the glass of the insulation material has a glass composition containing no $Ta_2O_5$ or containing $Ta_2O_5$, where the proportion of $Ta_2O_5$ in the glass composition is less than 2 percent by weight, optionally less than 1 percent by weight, optionally less than 0.5 percent by weight. This may be advantageous for reasons of cost among others.

The glass of the insulation material may also have a glass composition containing no $Nb_2O_5$ or containing $Nb_2O_5$, where the proportion of $Nb_2O_5$ in the glass composition is less than 2 percent by weight, optionally less than 1 percent by weight, optionally less than 0.5 percent by weight. This may be advantageous for reasons of cost among others. Moreover, an excessively high proportion of $Nb_2O_5$ can have an adverse effect on vitrification as a result of polyvalency.

There follows a specification of further components that are advantageously not present, essentially not present or present merely to a limited degree in relation to the glass composition, especially with regard to the avoidance of cytotoxicity.

In particular, it may be the case that the glass of the insulation material has a glass composition containing no PbO or containing PbO, where the proportion of PbO in the glass composition is less than 0.05 percent by weight, optionally less than 0.03 percent by weight, optionally less than 0.01 percent by weight. The glass may thus especially be essentially free of PbO.

In addition, it may be the case that the glass of the insulation material has a glass composition containing no BaO or containing BaO, where the proportion of BaO in the glass composition is less than 10 percent by weight, optionally less than 7 percent by weight, optionally less than 5 percent by weight. The glass may especially be essentially free of BaO. This may be advantageous with regard to the avoidance of toxicity.

The glass of the insulation material may also have a glass composition containing no $V_2O_5$ or containing $V_2O_5$, where the proportion of $V_2O_5$ in the glass composition is less than 0.5 percent by weight, optionally less than 0.3 percent by weight, optionally less than 0.1 percent by weight. This may be advantageous both with regard to the avoidance of toxicity and for reasons of cost.

In addition, the glass of the insulation material may have a glass composition containing no $Bi_2O_3$ or containing $Bi_2O_3$, where the proportion of $Bi_2O_3$ in the glass composition is less than 2 percent by weight, optionally less than 1 percent by weight, optionally less than 0.5 percent by weight. This may be advantageous with regard to the reaction with platinum.

It may also be the case that the glass of the insulation material has a glass composition containing no $WO_3$ or containing $WO_3$, where the proportion of $WO_3$ in the glass composition is less than 2 percent by weight, optionally less than 1 percent by weight, optionally less than 0.5 percent by weight. This may be advantageous with regard to the avoidance of components having a readily variable oxidation state.

Moreover, the glass of the insulation material may have a glass composition containing no $MoO_3$ or containing $MoO_3$, where the proportion of $MoO_3$ in the glass composition is less than 2 percent by weight, optionally less than 1 percent by weight, more optionally less than 0.5 percent by weight. This may be advantageous with regard to the avoidance of components having a readily variable oxidation state.

In general, avoidance of polyvalent components may be advantageous, and therefore envisaged, owing to interaction with the environment, some of it unknown.

In relation to the coefficient of thermal expansion (CTE) of the glass, it may be the case that the glass of the insulation material has a CTE (20° C.; 300° C.) in the range from 5 to 10 ppm/K, optionally in the range from 6 to 9 ppm/K, optionally in the range from 7 to 8 ppm/K.

This can especially achieve a matching of the material with titanium or titanium alloys, which can in turn improve the imperviousness of the feedthrough, especially hermetic imperviousness.

The glass of the insulation material may have a density in the range from 2.30 to 2.45 g/cm$^3$, optionally in the range from 2.32 to 2.43 g/cm$^3$, particularly in the range from 2.33 to 2.42 g/cm$^3$.

It may further be the case that the glass of the insulation material has a glass transition temperature $T_g$ of lower than 590° C., optionally lower than 570° C., optionally lower than 550° C.

In particular, the glass of the insulation material may have a glass transition temperature $T_g$ in the range from 440 to 590° C., optionally in the range from 460 to 570° C., particularly in the range from 480 to 550° C. In principle, a lower glass glass transition temperature $T_g$ may be advantageous with regard to processing.

In one development, the feedthrough, in addition to electrical signal transmission via electrical conductor, can also enable optical signal transmission.

In particular, the insulation material for this purpose, from one outer surface to the other, along the passage opening that runs through the main body, may have a transmittance $T_{vis}$ for at least one wavelength in the spectral range from 380 nm to 780 nm of at least 25%, optionally of at least 50%, optionally of at least 75%.

The feedthrough may also include an optical interface for transmission of light through the insulation material along the passage opening that runs through the main body.

The insulation material is optionally free of graphite particles on at least one outer face, especially in that the insulation material has been melted into the passage opening without application of pressure to the outer face, especially without exertion of pressure by charcoal weights on the outer face.

In relation to hermeticity, it may be the case that the insulation material accommodated in the passage opening of the main body is in contact with the main body and/or with the at least one electrical conductor in such a way that the contact face between the insulation material and the main body and/or the feedthrough has a hermeticity characterized by a helium leakage rate of less than $1 \cdot 10^{-8}$ mbar·l/s, optionally of less than $1 \cdot 10^{-9}$ mbar·l/s, optionally of less than $1 \cdot 10^{-10}$ mbar·l/s.

The hermeticity of feedthroughs may be verified, for example, by a helium leak test.

The feedthrough optionally has a multitude of electrical conductors that extend through the insulation material accommodated in the passage opening, optionally at least 2 electrical conductors, optionally at least 10 electrical conductors.

The main body may include a multitude of passage openings each incorporating insulation material, wherein at least one, especially exactly one, electrical conductor extends through the insulation material of each passage opening.

The main body including titanium or a titanium alloy may be in sheetlike form. The main body may have a first surface and an opposite second surface, where the passage opening forms an inner wall that connects the first surface to the second. The main body may define a plane that runs parallel to the first and/or second surface. The main body may, in a direction that runs parallel to the first and/or second surface and/or runs in the aforementioned plane, have a dimension greater than the diameter of the passage opening, especially at least twice as large, especially at least three times as large.

The insulation material present in the passage opening may have a contact angle of less than 90° on either side of the main body, i.e. both on the first surface side and on the second surface side, especially a contact angle with the values given further up. The insulation material may be set back with respect to the first and/or second surface of the main body. In other words, the insulation material may be accommodated in the passage opening in such a way that there is a step to the main body at the site of the inner wall.

The main body may have a thickness at right angles to its plane which is greater than the thickness of the insulation material at the inner wall of the passage opening. The main body may also have that thickness over an extended dimension along the first and/or second surface and/or the plane; for example, the main body may have that thickness at least in the region of twice the diameter of the passage opening, especially in the region of three times the diameter.

The conductor that extends through the insulation material may protrude beyond the insulation material and/or beyond the main body on one or both sides. In particular, the conductor may protrude with respect to the first and/or second surface of the main body. The excess on one or both sides may be greater than the thickness of the main body at the inner wall, especially at least twice as great, especially at least three times as great. The excess on one side may be greater than on the other side, especially at least twice as great, especially at least three times as great.

The present invention relates more particularly to a feedthrough for an implant and/or to an implant including a feedthrough as described above, wherein the glass of the insulation material is non-cytotoxic, especially in a standard determination according to EN ISO 10993-5 (July 2009 version).

In this connection, but also generally in principle, it may be the case that the feedthrough has at least two electrical conductors spaced apart by less than 5 mm, optionally less than 1 mm.

In addition, in this connection, but also generally, it may be the case that the greatest dimension of the passage opening running through the main body at right angles to the axis of the electrical conductor is less than 10 mm, optionally less than 2 mm.

The present invention further relates more particularly to a feedthrough for an oil/gas exploration device and/or to an oil/gas exploration device including a feedthrough as described above, wherein the feedthrough has a shock resistance of at least 100 g, optionally of at least 500 g, optionally of at least 750 g, and/or withstands such a shock with retention of its hermeticity, especially the hermeticity as described above.

In addition, in this connection, but also generally in principle, it may be the case that the feedthrough has a vibration resistance of at least 20 g rms, optionally of at least 40 g rms, optionally of at least 60 g rms, and/or withstands such a vibration with retention of its hermeticity, especially the hermeticity as described above.

In addition, in this connection, but also generally in principle, it may be the case that the main body is non-magnetic.

The present invention may also relate more particularly to a feedthrough for a wearable device and/or to a wearable device including a feedthrough as described above.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1:
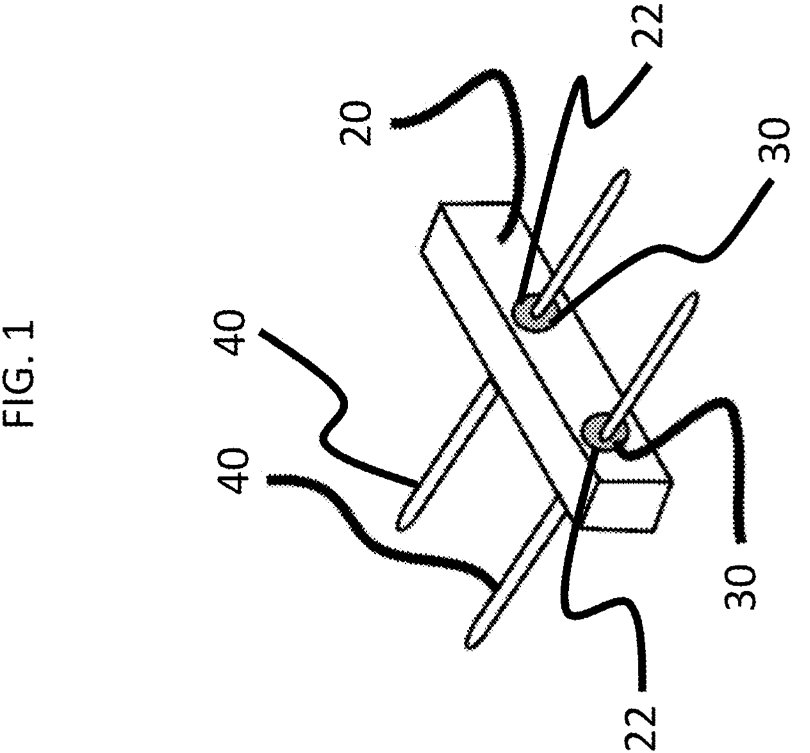
FIG. 1 is a schematic diagram of a feedthrough according to a first embodiment.

With reference to FIG. 1, a feedthrough has an outer main body 20, through which one or more passage openings 22 (two here) run, wherein each passage opening 22 accommodates an insulation material 30, through which at least one electrical conductor 40 extends. The conductor here may project out of the insulation material at one or both ends (at both ends here). The feedthrough shown has two internal conductors (pins) and can therefore be referred to as a 2-pole feedthrough. It is possible that the main body 20 serves as outer conductor and hence forms a further electrical conductor.

Figure 2:
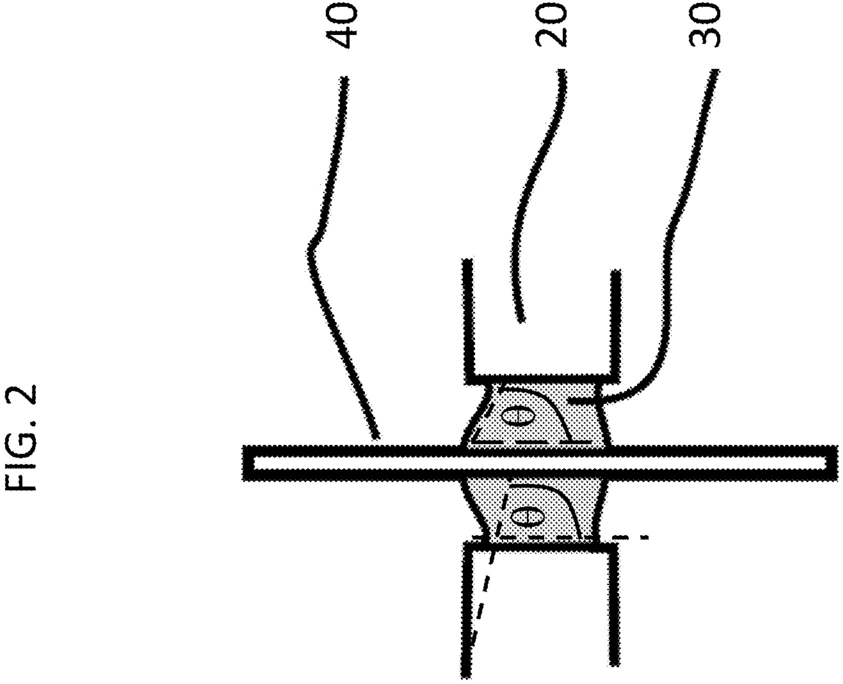
FIG. 2 is a schematic diagram of the feedthrough shown in FIG. 1 in cross section, showing the contact angle between the insulation material and the main body or electrical conductor.

With reference to FIG. 2, the insulation material 30 accommodated in the passage opening 22 has a contact angle $\theta$ of less than 90 degrees with respect to the surrounding main body 20. In addition, the insulation material 30 may optionally also have a contact angle $\theta'$ of less than 90° with respect to the electrical conductor 40. In principle, a weight, for example a charcoal mold, may be used in the melting of the insulation material 30 into the passage opening 22, in order to achieve the, or particular, contact angles $\theta$ or $\theta'$. However, this can sometimes be impractical in the case of a relatively high number of pins. It is alternatively possible that the insulation material is melted into the passage opening 22 in such a way that the contact angle $\theta<90°$ is formed merely because of the wetting properties of the insulation material on the main body material, such that it is possible to dispense with any weight, and the outer surface of the insulation material 30 is free of charcoal particles. The term “contact angle” is in particular synonymous with the term “wetting angle”.

Figure 4:
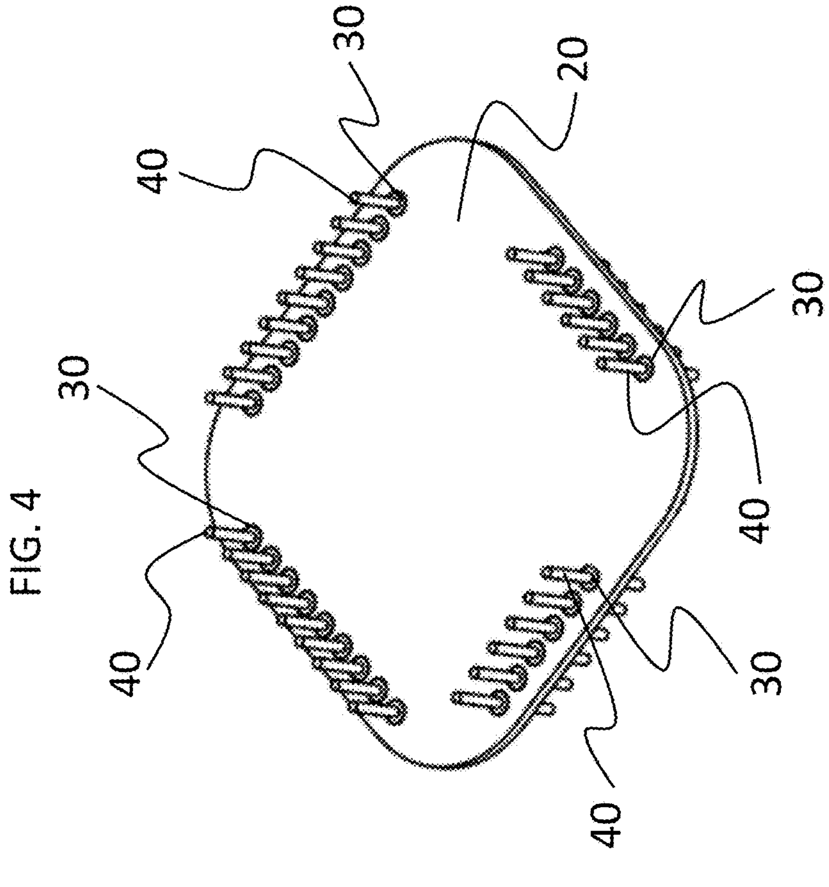
FIG. 4 is a schematic diagram of a feedthrough according to a third embodiment.
Figure 3:
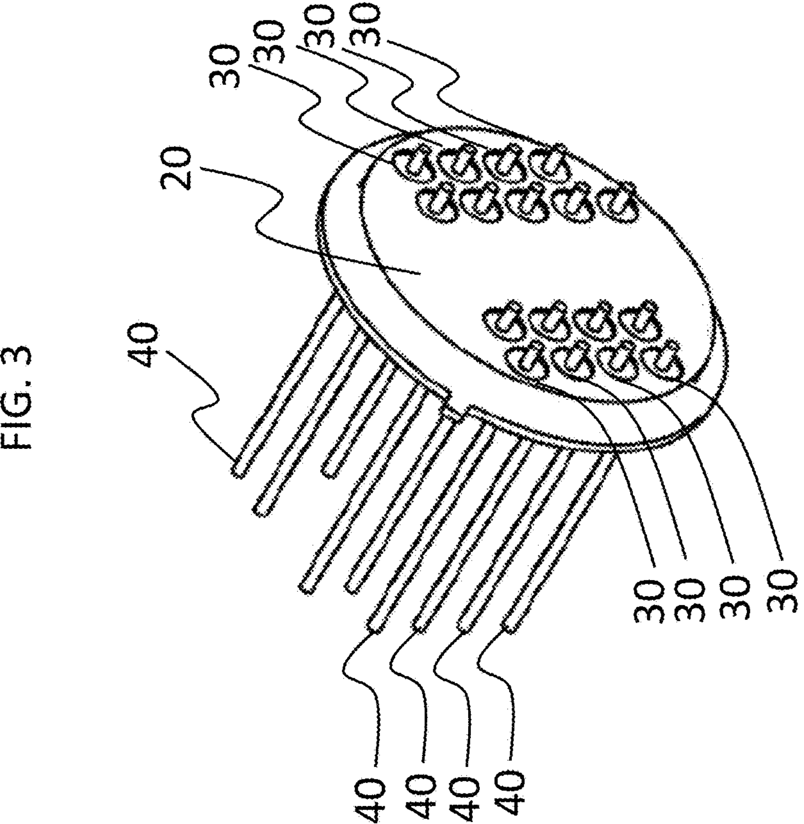
FIG. 3 is a schematic diagram of a feedthrough according to a second embodiment.

With reference to FIGS. 3 and 4, a feedthrough may also have a multitude of internal conductors (pins), such that, for example, a 17-pole feedthrough (FIG. 3) or even a 30-pole feedthrough (FIG. 4) may be provided. In the plug connectors shown, each individual internal conductor 40 extends through the insulation material of a single passage opening 22. However, it is also possible that a plurality or multitude of electrical conductors extend through the same insulation material in the same passage opening 22.

With regard to wetting of the insulation material 30 on the main titanium body 20 with a contact angle $\theta<90°$ (without use of weights), the insulation material 30 may especially take the form of a high-borate glass. It may be the case, for example, that the glass of the insulation material has a glass composition containing $B_2O_3$ and $SiO_2$, where the ratio of the proportion of $B_2O_3$ in percent by weight to the proportion of $SiO_2$ in percent by weight is at least 0.36, and/or that the glass of the insulation material has a glass composition containing $B_2O_3$, where the proportion of $B_2O_3$ in the glass composition is at least 20 percent by weight.

Especially for a high-borate glass and/or a glass composition having the abovementioned boron contents, it may be advantageous that the glass of the insulation material has a softening temperature of not more than 680° C., a sphere temperature of not more than 780° C., a hemisphere temperature of not more than 850° C. and/or a flow temperature of not more than 950° C., optionally not more than 940° C., optionally not more than 900° C.

It may especially be the case that the glass of the insulation material can be vitrified at temperatures below 950° C., optionally below 940° C. This results in the optional limitation in the characteristic feature of flow point from the established method of heating microscopy (EHM) to not more than 940° C.

In the case of vitrification in titanium or titanium alloys, it should be ensured that this process is optionally not conducted too far above, or is optionally conducted below, the temperature range of the α/β phase transition of titanium.

In one working example, the insulation material may include a glass having the following composition in % by weight:

| | |
|---|---|
| $SiO_2$ | 35-55% |
| $B_2O_3$ | 20-33% |
| $Al_2O_3$ | 3-23% |
| $Na_2O$ | 5-20% |
| CaO | 0-12% |
| $TiO_2$ | 0-10%. |

In a further working example, the insulation material may include a glass having the following composition in % by weight:

| | |
|---|---|
| $SiO_2$ | 40-51% |
| $B_2O_3$ | 24-30% |
| $Al_2O_3$ | 7-19% |
| $Na_2O$ | 10-17% |
| CaO | 0-7% |
| $TiO_2$ | 0-7%. |

In further working examples, the insulation material may include a glass having the aforementioned compositions, but including the following proportion of $B_2O_3$ in % by weight: 25.0-28.6.

In further working examples, the insulation material may include a glass having the aforementioned compositions, but including the following proportion of MgO in % by weight: less than 5.5, especially less than 5, especially than 4.5.

In specific working examples, the insulation material may include a glass having one of the following compositions in % by weight (glass 1 to 5):

| % by wt. | Glass 1 | Glass 2 | Glass 3 | Glass 4 | Glass 5 |
|---|---|---|---|---|---|
| $SiO_2$ | 42 | 49.8 | 41.1 | 46.8 | 46 |
| $Al_2O_3$ | 17 | 9.2 | 16.4 | 8.2 | 12 |
| $B_2O_3$ | 26 | 25.8 | 25.4 | 28.2 | 26 |
| $Na_2O$ | 15 | 15.1 | 11.4 | 12.8 | 12 |
| CaO | | | 6 | 4 | |
| $TiO_2$ | | | | | 4 |
| Total: | 100.0 | 99.9 | 100.0 | 100 | 100 |
| $B_2O_3$ / $SiO_2$ | 0.619 | 0.518 | 0.618 | 0.603 | 0.565 |

For the working examples glass 1 to glass 5, the following glass properties and powder properties were ascertained by heating microscopy (EHM):

| | Glass 1 | Glass 2 | Glass 3 | Glass 4 | Glass 5 |
|---|---|---|---|---|---|
| CTE(20;300° C.) [ppm/K] | 8.49 | 7.9 | 7.31 | 7.42 | 7.33 |
| Density [g/cm$^3$] | 2.336 | 2.383 | 2.411 | 2.412 | 2.335 |
| Tg [° C.] | 495 | 528 | 544 | 535 | 485 |
| Ew [° C.] | | 658 | 673 | 656 | 647 |
| EHM: | | | | | |
| sintering [° C.] | 577 | 544 | | 555 | 525 |
| Softening [° C.] | 643 | 670 | 675 | 670 | 663 |
| Sphere [° C.] | 764 | 723 | 740 | 719 | 725 |
| Hemisphere [° C.] | 843 | 801 | 828 | 806 | 836 |
| Flow temp. [° C.] | 926 | 864 | 907 | 864 | 906 |

For glass 1 to glass 5, storage of sintered specimens in 0.9% saline solution at 37.5° C.:

| Weight loss | Glass 1 | Glass 2 | Glass 3 | Glass 4 | Glass 5 |
|---|---|---|---|---|---|
| 1 d | | 0.003% | 0.005% | | |
| 2 d | | 0.01% | 0.003% | | |
| 3 d | | 0.01% | 0.005% | | |
| 4 d | 0.00% | 0.02% | 0.060% | | 0.00% |
| 5 d | | | | | |
| 6 d | | | | 0.00% | |
| 7 d | | | | 0.03% | 0.00% |
| 24 d | 0.0% | n.d. | | | |

For glass 1 to glass 5, properties of sintered specimens:

| Weight loss [%] | Glass 1 | Glass 2 | Glass 3 | Glass 4 | Glass 5 |
|---|---|---|---|---|---|
| Cold etch (HF) | 1.51 | 0.08 | 1.84 | 0.6 | 0.7 |
| HCl | 4.22 | 1.2 | 1.2 | 1.1 | 0.4 |
| Strike Ni | 0.78 | 0.57 | 0.41 | 0.1 | 0.1 |
| Acidic before Au | 0.96 | 0.91 | 0.89 | 0.1 | 0.1 |
| H2O - pure | 0 | 0.1 | 0 | 0 | 0.1 |
| Hot degreas | 0.05 | 0.09 | 0.05 | 0 | 0 |

The data in the table above suggests that glasses 2 to 5 have higher "galvanic stability" than glass 1. What is meant by "galvanic stability" is essentially stability to the aqueous chemicals used in typical galvanic pretreatment and coating processes (acids, alkalis and electrolytes). Hot degreas represents a hot wash liquor for degreasing.

The glass of the insulation material may also have been admixed with coloring components, e.g. CoO, or pigments, for example spinel-based pigments.

It is further possible that the glass includes fillers, for example low-expansion fillers, e.g. cordierite. A proportion of low-expansion fillers can make it possible under some circumstances to lower the coefficient of thermal expansion of the glass.

For example, with a proportion of 11% cordierite (melt for production of cordierite as filler), the lowering in the coefficient of thermal expansion (CTE) of glass 2 can be set to a value of about 7.0 ppm/K, especially without significant loss in the relevant properties.

For a saline solution test, the test object is produced from glass powder (like the compacts). The glass powder is stirred with demineralized water until small lumps form, which are then pressed manually into cylinder shape and sintered under nitrogen about 30 to 40° C. above the "sphere" temperature. The test objects usually weigh 0.5 g. The saline solution has a strength of 0.9%. About 120 ml of saline solution is warmed to about 37° C. in a beaker.

The test object lies at the edge of the beaker. A magnetic stirrer is set such that the saline solution is clearly in motion, but the test object is not moved. The beaker is covered with a glass lid, such that barely any concentration differences arise owing to evaporation. The test object is weighed before the test and once per day, and the relative loss of mass is used as a comparative value.

Some comparative glasses (Comp. 1 to 4) are specified hereinafter, which were characterized by the same methods as the abovementioned examples glass 1 to glass 5.

Comparative Glasses: Composition in % by Weight:

| % by wt. | Comp. 1 | Comp. 2 | Comp. 3 | Comp. 4 |
|---|---|---|---|---|
| $SiO_2$ | 7.3 | 47.7 | | |
| $Al_2O_3$ | 18.6 | 4.5 | 16.2 | 30 |
| $B_2O_3$ | 25.1 | 15.8 | 24.9 | 42 |
| $Na_2O$ | | 7.45 | | |
| $K_2O$ | | 0.4 | | |
| CaO | 14 | 14.3 | 7.2 | 16 |
| MgO | 7.9 | | | 12 |
| SrO | 6.8 | | | |
| $ZrO_2$ | | 9.33 | | |
| $TiO_2$ | | | 16.25 | |
| $La_2O_3$ | 20.3 | | 35.5 | |

Comparative Glasses: Glass Properties and Powder Properties by Heating Microscopy (EHM):

| | Comp. 1 | Comp. 2 | Comp. 3 | Comp. 4 |
|---|---|---|---|---|
| CTE(20; 300° C.) [ppm/K] | 7.8 | 7.0 | 7.1 | 6.2 |
| Density [g/cm$^3$] | 3.19 | 2.68 | 3.62 | 2.6 |
| Tg [° C.] | 620 | 612 | 643 | 617 |
| Ew [° C.] | 718 | 732 | 726 | 718 |
| EHM: | | | | |
| Softening [° C.] | 722 | 760 | 738 | |
| Sphere [° C.] | 746 | 797 | | |
| Hemisphere [° C.] | 845 | 883 | 1031 | |
| Flow temp. [° C.] | 909 | 953 | 1094 | |

Sintered Specimens of Comparative Glasses: Storage in 0.9% Saline Solution at 37.5° C.:

| Weight loss [%] | Comp. 1 | Comp. 2 |
|---|---|---|
| 1 d | 0.32 | 0.016 |
| 2 d | 0.46 | 0.032 |
| 3 d | 0.47 | 0 |
| 4 d | 0.70 | 0.020 |

Comparative Examples: Properties of Sintered Specimens

| Weight loss [%] | Comp. 1 | Comp. 2 |
|---|---|---|
| Cold etch (HF) | 0.21 | 0.36 |
| HCl | 0.57 | 0 |
| Strike Ni | 0.11 | 0 |
| Acidic before Au | 0.16 | 0.01 |
| H2O - pure | 0 | 0.01 |
| Hot degreas | 0 | 0.03 |

Storage of the comparative glass Comp. 1 in saline solution shows that a more than 10-fold weight loss occurs by comparison with the abovementioned glasses.

This insufficient stability on storage in NaCl solution shows that this Comp. 1 can be considered unsuitable for use in contact with body fluids, depending on the specification.

Characterization by EHM shows that Comp. 2 with a hemisphere temperature of about 880° C. and a flow temperature of 953° C. can be considered to be on the borderline for an optional feedthrough. In experiments, a vitrification temperature of about 980° C. was required for production of feedthroughs.

Characterization by EHM indicates that Comp. 3 with a hemisphere temperature well above 1000° C. cannot be vitrified at lower temperatures or, for example, temperatures below 900° C.

The glass Comp. 4 showed unsatisfactory adaptation to titanium; this type of glass spreads poorly on titanium. In the case of poor spreading and/or inadequate wetting, pressure may be needed, for example in the form of weights. However, such a course of action is less optional since it is more complex, especially for miniaturized designs and/or designs with complex pole geometries, for example designs with a multitude of electrical conductors and small distances between those conductors and/or designs with a multitude of electrical conductors, for example more than 10 electrical conductors.

Glasses 1 to 5 and comparative glasses 1 and 2 (without use of weights) have a wetting angle or contact angle on titanium of less than 90° C. This has a number of advantages in the production of feedthroughs. There is no need to press carbon dies onto the glass in order to achieve desired surface forms; soiling and sticking of carbon dies on glass surfaces (which can cause insulation problems) are avoided; and differences in coefficients of thermal expansion between carbon fixings and metal components do not constitute a barrier in the design of melt fixings.

The test glasses and comparative glasses were produced by melting the glasses on a 11 scale and forming them to castings, and also to ribbons of width about 1-2 cm. The cooled castings were used for purposes including determining the density, the coefficient of linear thermal expansion in the range from 20° C. to 300° C., i.e. CTE (20; 300° C.), and the fixed viscosity points $T_g$ and Ew by methods familiar to the person skilled in the art.

The coefficient of linear thermal expansion CTE was determined in the range of 20 to 300° C. from determination of the length change characteristics on solid-state bodies of length 100 mm by dilatometry.

Density was determined by measurement of buoyancy.

The softening temperature Ew (i.e. the temperature at which the lg of viscosity [dPas] is 7.6) was determined by viscometry on a square thread.

In order to ascertain the powder properties, ribbons of the test glasses were ground to a defined grain size (K3) and then characterized.

A generally customary method for determination of the vitrification-relevant temperatures is the method of heating microscopy (EHM).

In addition, the powders were sintered and characterized. The weight loss was ascertained on sintered specimens after exposure to chemical solutions, which represents the different treatments in galvanic processes.

In order to determine galvanic stability, compacts were produced from the ground powders of the test glasses and sintered. These sintered samples were then immersed in baths that simulate galvanic treatment, and the loss of mass was determined.

In order to determine stability in saline solution, the sintered specimens were stored in 0.9% saline solution at 37.5° C. for a period of 1-24 days. The loss of mass was then determined.

In order to determine cytotoxicity, the test for a cytotoxic effect of the test glasses was conducted according to standard EN ISO 10993-5: Test for in vitro cytotoxicity. No cytotoxic effect was detected for the glasses of the present invention.

In the production of feedthroughs, cleaning and coating in galvanic baths can be implemented, especially in order to improve functionalities such as weldability, bondability and solderability. The individual components, especially the glass used, are therefore optionally designed to be stable in such baths.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A feedthrough, comprising:

a main body including at least one passage opening running through the main body, the main body including titanium or a titanium alloy;

an insulation material accommodated in the at least one passage opening running through the main body, the insulation material including glass, the insulation material having a contact angle of less than 90 degrees in at least a portion of the insulation material with respect to the main body, the glass of the insulation material has a glass composition including $B_2O_3$ and $SiO_2$, wherein a ratio of a proportion of $B_2O_3$ in percent by weight to a proportion of $SiO_2$ in percent by weight is between 0.45 and 0.65; and at least one electrical conductor extending through the insulation material accommodated in the at least one passage opening.

2. The feedthrough according to claim 1, wherein at least one of:

(a) the contact angle of the insulation material with respect to the main body is between 56 and 86 degrees; and (b) the insulation material at least in a plurality of regions of the insulation material has a contact angle with respect to the at least one electrical conductor of between 56 and 86 degrees.

3. The feedthrough according to claim 1, wherein:

(a) the glass of the insulation material has a glass composition including $B_2O_3$, wherein a proportion of $B_2O_3$ in the glass composition is at least 21 percent by weight; or (b) the glass of the insulation material has a glass composition including $B_2O_3$, wherein a proportion of $B_2O_3$ in the glass composition is between 21 and 33 percent by weight.

4. The feedthrough according to claim 1, wherein at least one of:

(a) the glass of the insulation material has a softening temperature of not more than 750° C.;

(b) the glass of the insulation material has a sphere temperature of not more than 850° C.;

(c) the glass of the insulation material has a hemisphere temperature of not more than 950° C.;

(d) the glass of the insulation material has a flow temperature of not more than 1050° C.; and (e) the glass of the insulation material is stable on storage in a saline solution at 37.5° C.

5. The feedthrough according to claim 1, wherein:

(a) the glass of the insulation material has a glass composition including $Al_2O_3$, wherein a proportion of $Al_2O_3$ in the glass composition is at least 3 percent by weight; or (b) the glass of the insulation material has a glass composition including $Al_2O_3$, wherein a proportion of $Al_2O_3$ in the glass composition is between 3 and 17 percent by weight.

6. The feedthrough according to claim 1, wherein the glass of the insulation material has a glass composition including $Na_2O$, wherein a proportion of $Na_2O$ in the glass composition is at least 10 percent by weight.

7. The feedthrough according to claim 1, wherein at least one of:

(a) the glass of the insulation material has a glass composition including CaO, wherein a proportion of CaO in the glass composition is at most 11 percent by weight; and (b) the glass of the insulation material has a glass composition including $TiO_2$, wherein the proportion of $TiO_2$ in the glass composition is at most 10 percent by weight.

8. The feedthrough according to claim 1, wherein at least one of:

(a) the glass of the insulation material has a glass composition including no $K_2O$ or including $K_2O$, wherein a proportion of $K_2O$ in the glass composition is less than 7 percent by weight; and (b) the glass of the insulation material has a glass composition including no $LiO_2$ or including $LiO_2$, wherein a proportion of $LiO_2$ in the glass composition is less than 2 percent by weight.

9. The feedthrough according to claim 1, wherein at least one of:

(a) the glass of the insulation material has a glass composition including no MgO or including MgO, wherein a proportion of MgO in the glass composition is less than 10 percent by weight; and (b) the glass of the insulation material has a glass composition including no $ZrO_2$ or including $ZrO_2$, wherein a proportion of $ZrO_2$ in the glass composition is less than 0.9 percent by weight.

10. The feedthrough according to claim 1, wherein at least one of:

(a) the glass of the insulation material has a glass composition including no $La_2O_3$ or including $La_2O_3$, wherein a proportion of $La_2O_3$ in the glass composition is less than 1.5 percent by weight;

(b) the glass of the insulation material has a glass composition including no $Ta_2O_5$ or including $Ta_2O_5$, wherein a proportion of $Ta_2O_5$ in the glass composition is less than 2 percent by weight; and (c) the glass of the insulation material has a glass composition including no $Nb_2O_5$ or including $Nb_2O_5$, wherein a proportion of $Nb_2O_5$ in the glass composition is less than 2 percent by weight.

11. The feedthrough according to claim 1, wherein at least one of:

(a) the glass of the insulation material has a glass composition including no PbO or including PbO, wherein a proportion of PbO in the glass composition is less than 0.05 percent by weight;

(b) the glass of the insulation material has a glass composition including no BaO or including BaO, wherein the proportion of BaO in the glass composition is less than 10 percent by weight; and (c) the glass of the insulation material has a glass composition including no $V_2O_5$ or including $V_2O_5$, wherein a proportion of $V_2O_5$ in the glass composition is less than 0.5 percent by weight.

12. The feedthrough according to claim 1, wherein at least one of:

(a) the glass of the insulation material has a glass composition including no $Bi_2O_3$ or including $Bi_2O_3$, wherein a proportion of $Bi_2O_3$ in the glass composition is less than 2 percent by weight;

(b) the glass of the insulation material has a glass composition including no $WO_3$ or including $WO_3$, wherein a proportion of $WO_3$ in the glass composition is less than 2 percent by weight; and (c) the glass of the insulation material has a glass composition including no $MoO_3$ or including $MoO_3$, wherein a proportion of $MoO_3$ in the glass composition is less than 2 percent by weight.

13. The feedthrough according to claim 1, wherein the glass of the insulation material has a coefficient of thermal expansion (20° C.; 300° C.) in a range from 5 to 10 ppm/K.

14. The feedthrough according to claim 1, wherein at least one of:

(a) the glass of the insulation material has a glass transition temperature $T_g$ lower than 590° C.; and (b) the glass of the insulation material has a glass transition temperature $T_g$ in a range from 440 to 590° C.

15. The feedthrough according to claim 1, wherein at least one of:

(a) the insulation material includes a first outer surface and a second outer surface, wherein the insulation material, from the first outer surface to the second outer surface, along the at least one passage opening that runs through the main body, has a transmittance $T_{vis}$ for at least one wavelength in a spectral range from 380 nm to 780 nm of at least 25%; and (b) the feedthrough includes an optical interface configured for transmitting light through the insulation material along the at least one passage opening that runs through the main body.

16. The feedthrough according to claim 1, wherein the insulation material includes at least one outer face and is free of a plurality of graphite particles on the at least one outer face.

17. The feedthrough according to claim 1, wherein the feedthrough includes a contact face, wherein the insulation material accommodated in the at least one passage opening of the main body is in contact at least one of with the main body and with the at least one electrical conductor in such a way that (i) the contact face between the insulation material and the main body and (ii) the feedthrough has a hermiticity characterized by a helium leakage rate of less than $1 \cdot 10^{-8}$ mbar·l/s.

18. The feedthrough according to claim 1, further comprising a plurality of the at least one electrical conductor that extends through the insulation material accommodated in the at least one passage opening.

19. The feedthrough according to claim 1, wherein at least one of:

(a) the glass of the insulation material is non-cytotoxic;

(b) the feedthrough includes at least two of the at least one electrical conductor which are spaced apart by less than 5 mm; and (c) a greatest dimension of the at least one passage opening running through the main body at a right angle to an axis of the at least one electrical conductor is less than 10 mm.

20. The feedthrough according to claim 1, wherein at least one of:

(a) the feedthrough at least one of (i) has a shock resistance of at least 100 g and (ii) withstands such a shock with retention of a hermeticity of the feedthrough; and (b) the feedthrough at least one of (i) has a vibration resistance of at least 20 g rms, and (ii) withstands such a vibration with retention of hermeticity of the feedthrough.

* * * * *